United States Patent [19]

Duggan

[11] 4,381,786

[45] May 3, 1983

[54] TUNABLE ECG SENSING FILTER FOR PACEMAKER

[75] Inventor: Stephen R. Duggan, Rosemount, Minn.

[73] Assignee: Medtronic, Inc., Minneapolis, Minn.

[21] Appl. No.: 239,669

[22] Filed: Mar. 2, 1981

[51] Int. Cl.³ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,949,758 | 4/1976 | Jirak | 128/419 PG |
| 4,192,316 | 3/1980 | Walters et al. | 128/419 PG |
| 4,202,342 | 5/1980 | Keller, Jr. | 128/419 PG |
| 4,318,411 | 3/1982 | Elmqvist | 128/419 PG |

FOREIGN PATENT DOCUMENTS 2053688 2/1981 United Kingdom ......... 128/419 PG

OTHER PUBLICATIONS

Weckler, Gene P., Reticon Corporation Technical Note No. 100, "A Tapped Analog Delay for Sampled Data Signal Processing".

Primary Examiner—William E. Kamm
Attorney, Agent, or Firm—Merchant, Gould, Smith, Edell, Welter & Schmidt

[57] ABSTRACT

A tunable electrocardiogram sensing filter for a pacemaker includes a tapped analog delay (40) having a plurality of tap load resistors (44) selected according to a tap weight function to give a bandpass characteristic. The electrical ECG from the heart pacemaker lead (11) is applied to an input (41) of the tapped analog delay, and is successively sampled and transferred from stage to stage through the delay under control of a clock (34). The filtered output (33) is obtained by summing the tap load resistors, and may be applied for resetting pacemaker timing and output circuits in a demand type pacemaker. In an implantable implementation of the invention, the clock is programmable to different frequencies, which allows scaling the bandpass characteristic of the filter upwards or downwards in frequency to accommodate different frequency component characteristics of the ECG's of individual patients.

5 Claims, 3 Drawing Figures

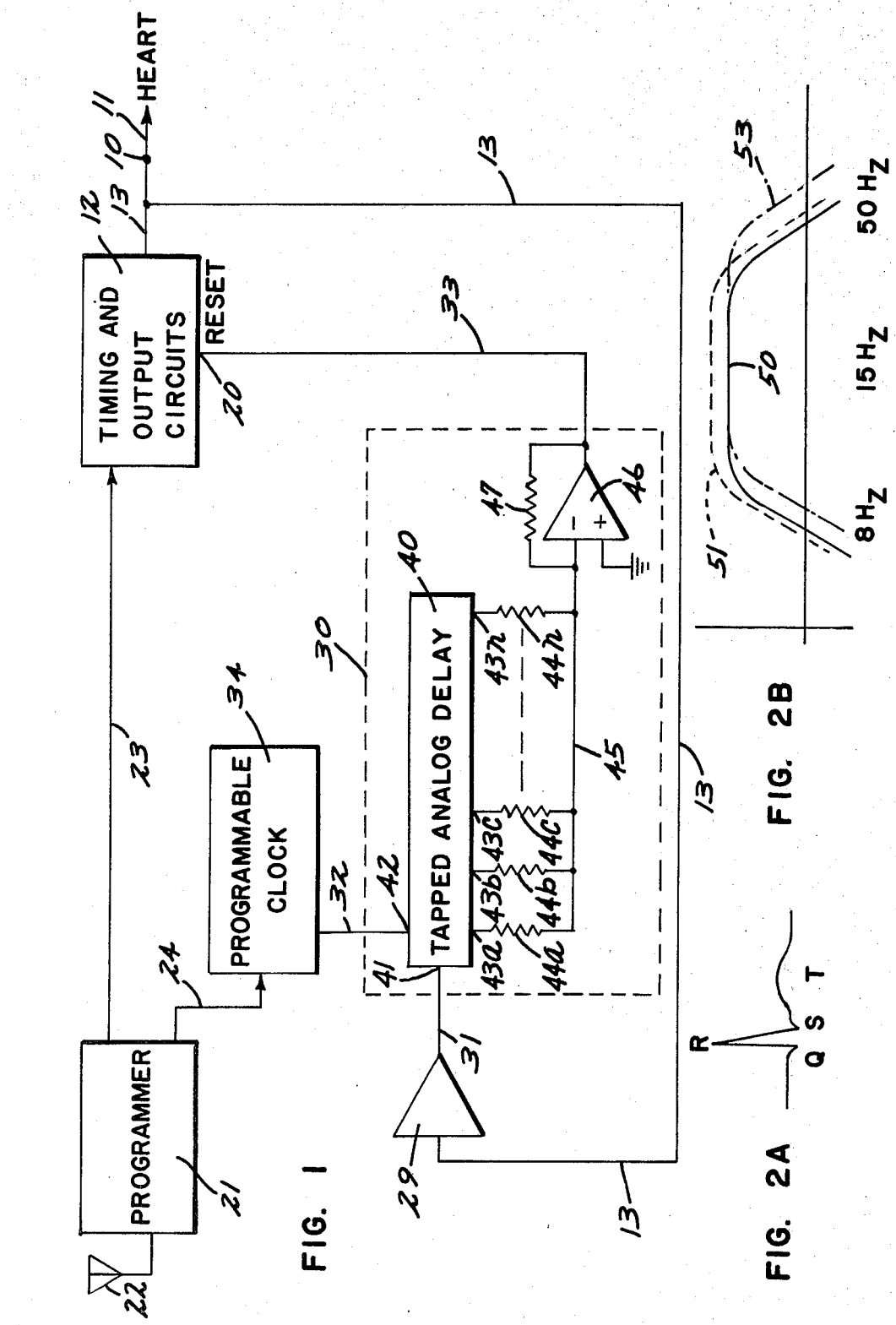

TUNABLE ECG SENSING FILTER FOR PACEMAKER

TECHNICAL FIELD OF THE INVENTION

The invention pertains to the field of artificial heart pacemakers, and particularly to pacemakers having sense amplifier circuits for detecting electrical signals indicative of contractions (depolarizations) of the heart. Specifically, the invention pertains to an electrical filter for detecting heart depolarizations wherein the filter characteristics can be tuned to match the electrocardiogram (ECG) of a given patient. In the case of an implantable pacemaker, the invention permits tuning of the filter by remote programming after implant.

BACKGROUND OF THE INVENTION

Artificial heart pacemakers are widely used in the medical field for the treatment of a number of different heart disorders. Many different types of pacemakers, operating in many different modes, have been developed over the years for the treatment of specific disorders or conditions. The control of the operation of most types of modern pacemakers depends in part on the reliable sensing of electrical signals from the patient's heart indicative of spontaneous contractions. For example, in various types of demand pacemakers, the decision whether to deliver a stimulating pulse to the heart is based upon whether a spontaneous heartbeat has occurred within a predetermined time interval from the preceding beat. The spontaneous beat is detected by electrical signals which are part of the ECG, generated within the heart and transmitted over the pacemaker lead to sense amplifier circuitry within the pacemaker. Upon detection of a spontaneous depolarization, the pacemaker timing circuits are reset and the output circuits are inhibited from delivering a stimulating pulse for that heartbeat cycle. Reliable detection of spontaneous heart depolarizations is important in demand type pacemakers in order to avoid unwanted and possibly harmful effects of competitive pacing. If the timing output circuits are not reset following a spontaneous contraction, there is a danger of delivering a stimulating pulse when none is needed. Further, the stimulating pulse might occur shortly after the spontaneous depolarization, during the vulnerable period of the ventricle.

It is generally necessary to provide some type of filtering circuits for the sensing amplifier in a demand pacemaker, so that it responds only to the desired portion of the ECG signals from the heart. For example, in the case of a demand pacemaker sensing and pacing in the ventricle of the heart, it is generally necessary that the pacemaker respond only to the R-wave, or QRS complex of the electrocardiogram indicative of a ventricular depolarization, and not any other signals originating in the heart or elsewhere that might be picked up by the ventricular lead. Examples of such other signals include 60 Hz noise, muscle noise, and spurious RF signals. Similarly, in the case of a pacemaker having a demand operation associated with the atrium, or in the case of an atrial synchronous pacemaker, it is important that the atrial sensing circuits respond only to the P-wave of the ECG which is indicative of an atrial depolarization. Filtering circuits are often used for both atrial and ventricular sensing circuits, but of course the filter characteristics would be different in each case since the frequency spectrums of P-waves and R-waves are different.

The widths of the P-waves and R-waves vary from patient to patient. The width affects the band of frequencies wherein the maximum energy content resides. Thus the frequency content of P-waves and R-waves varies from patient to patient. Furthermore, it is known that the width of the P-waves and R-waves may vary in time for a given patient. This is particularly true immediately after a myocardial infarction.

In the design of atrial or ventricular sensing amplifier filtering circuits, various types of filters such as multiple pole active filters have been used. Because of the variability of the frequency band of maximum energy in different patients, it has been necessary to use filtering circuits designed to provide a bandpass filter covering the entire frequency range for all patients. The bandwidth of the filter as well as the gain of the associated amplifying circuits are selected to give the required degree of sensitivity within the selected passband. Selecting the circuit parameters involves choices and compromises, because making the passband too wide opens the circuit up for extraneous signals, while making the passband too narrow carries the risk of failing to detect the P- or R-waves of some patients. Since it is impractical to custom design filtering circuits for pacemakers for different individuals, and since it has heretofore been impractical to provide a means for tuning the filter to the needs of a given patient, particularly in the case of an implantable pacemaker, it has therefore been necessary to provide a bandpass wide enough to pass the frequency components of all patients. The result has been that the filter characteristics are less than optimum for any given patient.

It will be appreciated that in the case of conventional electronic filters it would be necessary to change a great number of component values in order to change the bandpass characteristics, and this would require so many additional components and switches as to be impractical in an implantable pacemaker. Adding additional components usually has a serious negative impact on an implantable device in terms of current drain, battery life, physical size, circuit reliability, and cost.

A compromise design is often used for atrial and ventricular sensing filters, wherein the filter characteristics are designed to pass the P-waves or R-waves, respectively, of the majority of patients to be encountered, and a gain or sensitivity adjustment is provided to take care of patients whose frequency bands fall marginally at either end of the passband. While providing a workable solution, such a compromise still suffers the disadvantages of providing less than optimum filtering characteristics and excessive gain outside the P- or R-wave band for a given patient, which has the potential of making the sensing circuit susceptible to signals other than desired P- or R-waves picked up by the corresponding pacemaker lead.

The present invention solves the above-mentioned problems existing in the prior art by providing an ECG sensing filter for a pacemaker which is conveniently tunable to match the frequency ranges of interest (P-waves in the case of atrial sensing or R-waves in the case of ventricular sensing). It is particularly useful in implantable pacemakers, whereby the tuning can be done by remote programming after implantation. Further, in the case of patients who have suffered a myocardial infarction or who have had a change in width of the P- or R-waves for any other reason, the present invention provides for remote adjustability of the sense amplifier band pass to permit sensing which is optimal in that it maximizes the desired signal energy while minimizing undesired signal energy, i.e., noise.

SUMMARY OF THE INVENTION

The present invention provides a tunable ECG sensing filter for a pacemaker, including a transversal filter connected to receive the ECG signal from the pacemaker lead to the heart, and a programmable clock for providing clock signals to the transversal filter. The transversal filter, which includes an analog delay device, has a number of taps to which electrical loads are connected according to a tap-weight function to achieve a bandpass filtering characteristic at the output of the filter. The programmable clock is connected to a programmer within the pacemaker and is operative to change the clock frequency which is applied to the analog delay in response to external signals received by the programmer. Changing the clock frequency shifts the bandpass frequency of the filter, so that by selection of the appropriate clock frequency, the bandpass characteristics of the transversal filter can be shifted to match the ECG frequency component range of interest for a particular patient.

BRIEF DESCRIPTION OF THE DRAWING

In the drawing,
FIG. 1 is an electrical block diagram of a pacemaker using a tunable ECG sensing filter according to the present invention;
FIG. 2A is a waveform of a portion of an electrocardiogram; and
FIG. 2B is a graph showing bandpass characteristics for a sensing filter for a pacemaker.

DETAILED DESCRIPTION OF THE PREFERRED EMBODIMENTS

For purposes of explanation, the drawings and description of this invention are set forth herein in terms of ventricular sensing circuits, but it will be understood that the invention is equally applicable to atrial sensing, with appropriate changes in the frequency characteristics of the filter.

In FIG. 1, an implantable pacemaker includes a terminal 10 to which a lead 11 is connected. Lead 11 connects to the appropriate chamber of the heart, in this example the ventricle, as is generally known in the art. Inside the pacemaker, reference number 12 designates the timing and output circuits of the pacemaker which have all been grouped together in block 12 in the interests of clarity. Block 12 performs the functions of timing the escape interval between heartbeats, and providing an output pulse, if required, over conductor 13 which connects to terminal 10 and from there to the heart. Block 12 also has a reset input 20 which connects from the sensing amplifier and filter, described below, to cause resetting of the timing circuits resulting in inhibition of the output circuits upon detection of a timely spontaneous heart contraction within the selected escape interval. The design of specific circuits for the timing and output functions of a pacemaker are generally known, and since the specific timing and output circuit per se do not form part of the present invention, they are not shown in detail, but only in block form.

In the case of a programmable heart pacemaker, a programmer circuit 21 is provided. It includes an antenna 22 which is adapted to receive signals from an external programming device, in the form of RF or magnetic coded signals. Programmer 21 decodes the signals into various commands, as is generally known, for controlling operating parameters of the pacemaker, such as repetition rate (escape interval) pulse amplitude, pulse width and the like. The appropriate commands are transmitted via control line or lines 23 to the timing and output circuits 12 for controlling their appropriate function as is generally known in the art. A control line 24 connects from programmer 21 to a program input of a programmable clock 34.

A branch of conductor 13 connects to the sensing circuits for detecting depolarizations of the heart. Specifically, conductor 13 connects to the input of an amplifier 29, and the output of amplifier 29 connects through conductor 31 to filter 30. Filter 30 also receives a clock frequency input on conductor 32, and provides its output on conductor 33, which connects to reset input 20 of the timing and output circuits 12.

The primary component of filter 30 is a tapped analog delay 40, sometimes also referred to as a tapped analog shift register. Device 40 has a signal input 41, to which conductor 31 is connected, a clock input 42 to which conductor 32 is connected, and a plurality of taps 43a–43n. A plurality of load resistors 44a–44n connect from taps 43a–43n, respectively, to a summing node 45. Summing node 45 connects to the inverting input of a summing amplifier 46. The output of amplifier 46 connects to conductor 33, and a feedback resistor 47 connects from the output to the inverting input of amplifier 46.

Tapped analog delay 40 is a charge-transfer device having a plurality of n stages, for example 32 stages. The analog signal applied at input 41 is sampled and held in the first stage, then subsequently transferred to the second stage and successive stages on successive clock intervals applied at input 42. A plurality of analog levels representing a plurality of prior inputs are thus moving from stage to stage through delay device 40 on successive clock intervals. These analog levels are non-destructively tapped and applied through buffer amplifiers to taps 43a–43n which are spaced from each other one sample time apart along the delay. A commercially available tapped analog delay of this type is the TC-32A manufactured by Reticon Corporation of Sunnyvale, Calif. The filtering characteristics of delay 40 are determined by the values for tap load resistors 44, referred to as the tap weight function, and the frequency of the clock pulses applied at input 42. The theory and procedure for designing the tap weight function to achieve the desired filter characteristic are available in the art; for example, see Weckler, Gene P., "A Tapped Analog Delay for Sampled Data Signal Processing", Technical Note No. 100 Reticon Corporation, Sunnyvale, Calif. Briefly, various types of low-pass or bandpass filters can be realized through appropriate selection of the tap weight function. For use in the present invention, a bandpass function is utilized. The center frequency of the passband can then be shifted by changing the clock frequency.

FIG. 2A shows a simplified portion of an electrocardiogram such as might be picked up by the ventricular lead 11 in the heart, and transmitted thereover to the pacemaker and applied vai conductor 13 to the sensing and filtering circuits. Amplifier 29 provides initial amplification to bring the signal up to usable levels for filter 30, and may also provide clipping or limiting functions to protect delay device 40 from the voltage impulse appearing at conductor 13 during delivery of a stimulating pulse. Amplifier 29 can also be designed, through techniques generally known in the art, to provide a desired insensitive or refractory period following a stimulation pulse. The QRS complex of the waveform of FIG. 2A contains frequency components falling in a frequency band from approximately 8 hertz to approximately 50 hertz, centered at approximately 15 hertz. This band is indicated in FIG. 2B, where the horizontal axis indicates frequency, and the vertical axis indicates relative response. Curve 50 shows a desired bandpass characteristic for a ventricular sensing circuit in a pacemaker.

As previously mentioned, the shape of the QRS complex differs for different individuals, and while most individuals would have QRS frequency components falling within the passband of curve 50, for some individuals important frequency components would fall at the upper or lower margins. As previously mentioned, the prior art provides some accommodation for these extreme cases by providing a gain or sensitivity adjustment for the sensing amplifier. Increasing the gain would have the effect of moving the curve 50 to the position indicated by dotted line 51 in FIG. 2B. This would broaden the passband somewhat, but is subject to the disadvantage of providing excessive sensitivity for the middle of the passband, which increases the possibility of detecting spurious signals.

In contrast, the present invention allows for accommodating individuals whose QRS frequency components are unusually high or low, by shifting the bandpass curve 50 to higher or lower frequencies. This is accomplished by changing the clock frequency applied at input 42, without any need for changing the tap weight function values of resistors 44a–44n. This is accomplished through programmable clock 34, which is designed to provide several different clock frequencies in response to program code commands received via control line 24 from programmer 21. A remote programming device can therefore send programming signals to change the frequency of clock 34 to any of a number of preselected values, and the bandpass characteristic of filter 30 is accordingly shifted. For example, in FIG. 2B, broken line 53 shows the result of increasing the frequency of programmable clock 34, so as to shift the passband higher in frequency, while retaining the basic bandpass characteristic. In this manner, bandpass curve 50 can be scaled up or down in frequency to match or accommodate the individual characteristics of different patients without having to increase gain with its attendant unwanted side effects as mentioned above.

While the example discussed above is in terms of R-wave sensing from the ventricle of the heart, similar principles apply to P-wave sensing from the atrium in a pacemaker having atrial sensing. The tap weighting function and choice of clock frequencies would be selected in that case to correspond to the desired passband for physiological P-waves.

Thus, according to the present invention, there is provided an improved tunable ECG sensing filter for use in a pacemaker, which permits tuning the filter characteristic to accommodate individual variances in the frequency components of patients' ECG's. Particularly in the case of implantable pacemakers, this can be accomplished simply by programming different clock frequencies for the filter, without having to reprogram a large number of filter component values. Tuning of the filter to the characteristics of the individual patient provides for more reliable sensing of the selected portion of the electrocardiogram.

What is claimed:

1. A tunable electrocardiogram sensing filter for a heart pacemaker, comprising:
   a transversal bandpass filter having a signal input, a clock input, and a signal output;
   means for applying signals representing the patient's electrocardiogram to the input of the transversal filter;
   a variable frequency clock connected for applying clock pulses to the clock input of the transversal filter; and
   means for adjusting the frequency of the variable frequency clock to adjust the band pass frequencies of the transversal filter, thereby to permit tuning of the filter to match the frequency characteristics of the patient's electrocardiogram.

2. A tunable filter according to claim 1 wherein said pacemaker is an implantable pacemaker, and wherein said means for adjusting includes remotely programmable means for receiving programming signals for adjusting the frequency of the variable frequency clock, so that the filter can be tuned externally of the body in which the pacemaker is implanted.

3. A tunable electrocardiogram sensing filter according to claim 1 wherein said transversal filter comprises a tapped analog delay device, a summing amplifier, and a plurality of load resistors connecting the taps to the summing amplifier, the values of the resistors comprising a tap weight function to form a bandpass characteristic for the filter corresponding to a desired frequency band of the electrocardiogram.

4. A tunable electrocardiogram sensing filter for a heart pacemaker comprising:
   a tapped analog delay device having a signal input and a clock input and a plurality of taps;
   a summing amplifier;
   a plurality of load resistors connecting the taps of the analog delay device to the summing amplifier, said load resistors having values defining a tap weight function to form a bandpass characteristic for the filter;
   means connected for applying the patient's electrocardiogram signals from a lead terminal of the pacemaker to the signal input of the tapped analog delay device;
   a clock connected for providing clock signals to the clock input of the tapped analog delay; and
   means for adjusting the frequency of said clock to adjust the frequency of the passband of the filter.

5. An implantable demand pacemaker, comprising:
   terminal means for connection to a patient's heart;
   pulse generating means connected for periodically applying stimulating pulses to said terminal means for stimulating the patient's heart;
   a tapped analog delay device having a signal input, a clock input and a plurality of output taps;
   means connecting said terminal means to the signal input means for the tapped analog delay device for conveying electrical signals from the patient's heart thereto;
   a clock connected for providing clock signals to the clock input of said tapped analog delay device;
   a summing amplifier;
   a plurality of load resistors connecting the output taps of said analog delay device to the summing amplifier, said load resistors having values defining a tap weight function to form a bandpass filter characteristic for the tapped analog delay device;
remotely programmable means connected to said clock for adjusting the frequency thereof so that said bandpass frequency may be adjusted to match a range of frequency components of the patient's electrocardiogram; and
means connecting the output of said summing amplifier to said pulse generating means, and operable upon receipt of a signal from the summing amplifier indicating occurrence of a depolarization of the patient's heart to reset and inhibit said pulse generating means from delivering a stimulating pulse.

* * * * *